US011980357B2

(12) United States Patent
Sengun et al.

(10) Patent No.: US 11,980,357 B2
(45) Date of Patent: *May 14, 2024

(54) MULTI-PIECE ANCHOR INSERTER

(71) Applicant: Medos International Sarl, Le Locle (CH)

(72) Inventors: Mehmet Z. Sengun, Raynham, MA (US); Joseph Hernandez, Sandwich, MA (US); Gerome Miller, Randolph, MA (US)

(73) Assignee: Medos International Sarl, Le Locle (CH)

( * ) Notice: Subject to any disclaimer, the term of this patent is extended or adjusted under 35 U.S.C. 154(b) by 301 days.

This patent is subject to a terminal disclaimer.

(21) Appl. No.: 17/324,721

(22) Filed: May 19, 2021

(65) Prior Publication Data

US 2021/0267586 A1 Sep. 2, 2021

Related U.S. Application Data

(60) Continuation of application No. 16/022,289, filed on Jun. 28, 2018, now Pat. No. 11,013,505, which is a
(Continued)

(51) Int. Cl.
*A61B 17/04* (2006.01)
*A61B 17/00* (2006.01)

(52) U.S. Cl.
CPC .............. *A61B 17/0401* (2013.01); *A61B 2017/00477* (2013.01); *A61B 2017/0403* (2013.01);
(Continued)

(58) Field of Classification Search
CPC .............. A61F 2/0811; A61B 17/0401; A61B 2017/0409; A61B 2017/0414;
(Continued)

(56) References Cited

U.S. PATENT DOCUMENTS

| 4,838,264 A | 6/1989 | Bremer et al. |
| 5,100,417 A | 3/1992 | Cerier et al. |

(Continued)

FOREIGN PATENT DOCUMENTS

| CN | 101422381 A | 5/2009 |
| CN | 102525583 A | 7/2012 |

(Continued)

OTHER PUBLICATIONS

U.S. Appl. No. 13/728,181, filed Dec. 27, 2012.
(Continued)

*Primary Examiner* — Katherine M Shi
(74) *Attorney, Agent, or Firm* — Mintz, Levin, Cohn, Ferris, Glovsky and Popeo, P.C.

(57) ABSTRACT

Various devices, systems, and methods are provided for securing soft tissue to bone. In one exemplary embodiment, a two-piece inserter tool is provided that includes a tip portion that is configured to be removably coupled to a handle portion. A distal portion of the tip portion can be configured to be coupled to a suture anchor, and the tip portion and the anchor can be passed through a continuous suture loop prior to mating the tip portion to the handle portion.

19 Claims, 10 Drawing Sheets

Related U.S. Application Data continuation of application No. 14/926,652, filed on Oct. 29, 2015, now Pat. No. 10,034,664, which is a division of application No. 13/728,181, filed on Dec. 27, 2012, now Pat. No. 9,198,650.

(52) U.S. Cl.
CPC .............. *A61B 2017/0409* (2013.01); *A61B 2017/0412* (2013.01)

(58) Field of Classification Search
CPC ...... A61B 2017/0412; A61B 2017/044; A61B 2017/0445; A61B 2017/0427; A61B 2017/0458; A61B 2017/0496; A61B 2017/0403; A61B 2017/0438; A61B 2017/0456; A61B 2017/0464; A61B 17/0469
See application file for complete search history.

(56) References Cited

U.S. PATENT DOCUMENTS

| | | | |
|---|---|---|---|
| 5,141,520 | A | 8/1992 | Goble et al. |
| 5,824,011 | A | 10/1998 | Stone et al. |
| 5,899,920 | A | 5/1999 | DeSatnick et al. |
| 5,980,558 | A | 11/1999 | Wiley |
| 5,989,252 | A | 11/1999 | Fumex |
| 6,146,407 | A | 11/2000 | Krebs |
| 6,165,203 | A | 12/2000 | Krebs |
| 8,114,128 | B2 | 2/2012 | Cauldwell et al. |
| 9,198,650 | B2 | 12/2015 | Sengun et al. |
| 9,265,494 | B2 | 2/2016 | Hester et al. |
| 10,034,664 | B2 | 7/2018 | Sengun et al. |
| 11,013,505 | B2 | 5/2021 | Sengun et al. |
| 2001/0002440 | A1* | 5/2001 | Bonutti .............. A61B 17/0401 606/232 |
| 2002/0161401 | A1 | 10/2002 | Steiner |
| 2004/0039404 | A1* | 2/2004 | Dreyfuss ............ A61B 17/0401 606/148 |
| 2005/0149063 | A1 | 7/2005 | Young et al. |
| 2005/0187577 | A1 | 8/2005 | Selvitelli et al. |
| 2008/0004659 | A1 | 1/2008 | Burkhart et al. |
| 2008/0147063 | A1 | 6/2008 | Cauldwell et al. |
| 2008/0255613 | A1 | 10/2008 | Kaiser et al. |
| 2008/0306511 | A1 | 12/2008 | Cooper et al. |
| 2009/0076544 | A1 | 3/2009 | Dimatteo et al. |
| 2009/0149884 | A1 | 6/2009 | Snyder et al. |
| 2009/0312794 | A1 | 12/2009 | Nason et al. |
| 2010/0292732 | A1 | 11/2010 | Hirotsuka et al. |
| 2011/0152867 | A1 | 6/2011 | Petrzelka et al. |
| 2011/0313471 | A1 | 12/2011 | McLean et al. |
| 2012/0041484 | A1 | 2/2012 | Briganti et al. |
| 2012/0130423 | A1 | 5/2012 | Sengun et al. |
| 2012/0165864 | A1 | 6/2012 | Hernandez et al. |
| 2012/0179199 | A1 | 7/2012 | Hernandez et al. |
| 2012/0203340 | A1 | 8/2012 | Choinski et al. |
| 2012/0253391 | A1 | 10/2012 | Frey |
| 2013/0158599 | A1* | 6/2013 | Hester ................ A61B 17/0401 606/232 |
| 2014/0188165 | A1 | 7/2014 | Sengun et al. |
| 2016/0045196 | A1 | 2/2016 | Sengun et al. |
| 2018/0303475 | A1 | 10/2018 | Sengun et al. |

FOREIGN PATENT DOCUMENTS

| | | |
|---|---|---|
| EP | 1199035 A1 | 4/2002 |
| EP | 2036501 A2 | 3/2009 |
| EP | 2455003 A2 | 5/2012 |
| WO | 9625887 A1 | 8/1996 |
| WO | 2012088496 A2 | 6/2012 |

OTHER PUBLICATIONS

U.S. Appl. No. 14/926,652, filed Oct. 29, 2015.
U.S. Appl. No. 16/022,289, filed Jun. 28, 2018.
Extended European Search Report for EP App. No. 13199715.7 dated May 7, 2015, 8 pages.
Indian Examination Report for Indian App. No. 3594/DEL/2013 dated Dec. 19, 2019, 5 pages.
Japanese Office Action for Application No. 2013-268847, dated Sep. 26, 2017, 5 pages.

\* cited by examiner

MULTI-PIECE ANCHOR INSERTER

CROSS-REFERENCE TO RELATED APPLICATIONS

This application is a continuation of U.S. application Ser. No. 16/022,289 filed on Jun. 28, 2019, and entitled "Multi-Piece Anchor Inserter," which is a continuation of U.S. application Ser. No. 14/926,652 (now U.S. Pat. No. 10,034,664) filed on Oct. 29, 2015, and entitled "Multi-Piece Anchor Inserter," which is a divisional of U.S. application Ser. No. 13/728,181 (now U.S. Pat. No. 9,198,650) filed on Dec. 27, 2012, and entitled "Multi-Piece Anchor Inserter," which are hereby incorporated by reference herein in their entireties.

FIELD

The present invention relates generally to devices, systems, and methods for securing soft tissue to bone using a multi-piece anchor inserter.

BACKGROUND

Soft tissues, such as ligaments, tendons, and muscles, are attached to a large portion of the human skeleton. In particular, many ligaments and tendons are attached to the bones which form joints, such as shoulder and knee joints. A variety of injuries and conditions require attachment or reattachment of soft tissue to bone. For example, when otherwise healthy tissue has been torn away from a bone, surgery is often required to reattach the tissue to the bone to allow healing and natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone.

Proper attachment of soft tissue to bone requires that it be placed in the anatomically correct position to promote optimal healing. Conventional methods for attaching soft tissue to bone have typically used anchors through which a suture can be pulled to draw a piece of soft tissue attached to the suture into proximity of a surface of the bone after the anchor is inserted in a predrilled bone cavity. Such methods then require a free end or ends of the suture to be tied off to hold the soft tissue in place. More recently, however, "knotless" suture anchors have been utilized to eliminate the need to tie off the free end(s) of the suture. Many such "knotless" suture anchor systems control tension on tissue by a depth to which the anchor is driven into bone. Other "knotless" suture anchor systems utilize a sleeve that receives the anchor for locking the suture. Suture anchor systems with sliding knots for repairing torn or damaged tissue have also been traditionally utilized.

The soft tissue may be attached to the bone during open surgery, or during closed (e.g., arthroscopic) surgical procedures. Closed surgical procedures can be preferred since they are less invasive and are less likely to cause patient trauma. In a closed surgical procedure, a surgeon performs diagnostic and therapeutic procedures at a surgical site through small incisions, called portals, using instruments specially designed for this purpose. One problem encountered in the less invasive, closed surgical procedures is that the surgeon has significantly less room to perform the required manipulations at the surgical site than in open surgery. Thus, devices and methods are needed which will allow a surgeon to effectively and easily attach soft tissue to bone in the small spaces provided by less invasive surgical procedures.

Accordingly, there remains a need for improved devices, systems, and methods for securing soft tissue to bone.

SUMMARY

The present invention generally provides multi-piece anchor inserters and methods of use. In one aspect, a suture anchor system is provided that includes an anchor having proximal and distal ends with an inner lumen extending from the proximal end through at least a portion thereof, and an inserter tool having a handle portion and a separate tip portion. The anchor is configured to be implanted in bone. The tip portion has a proximal end configured to removably mate to a distal end of the handle portion and has a distal end configured to extend into at least a portion of the inner lumen in the anchor for removably mating the anchor to the tip portion of the inserter tool.

The system can vary in any number of ways. For example, the proximal end of the tip portion and the distal end of the handle portion can include complementary male and female mating elements configured to mate the tip portion to the handle portion. In one embodiment, the proximal end of the tip portion and the distal end of the handle portion can include threads formed thereon and configured to threadably mate to one another. In another embodiment, the proximal end of the tip portion and the distal end of the handle portion can mate by a snap-fit engagement. For example, one of the tip and the handle portion can include a protrusion that is configured to be received within a groove or recess in or on the other one of the tip and the handle portion to thereby mate the two components. For another example, the tip portion can include a shoulder formed thereon that is configured to abut a proximal-most end of the anchor when the distal end of the tip portion is inserted into the inner lumen in the anchor.

In some embodiments, the system can include a first suture extending through the inner lumen of the anchor and having a sliding knot formed thereon and positioned within the anchor. The first suture can have a free end extending from the anchor and a collapsible loop portion extending from the anchor. In an exemplary embodiment, the system can also include a second suture in the form of a continuous loop. The second suture can be slidably disposed on the collapsible loop portion of the first suture. The second suture can have a diameter that is in a range of about 5 mm to 40 mm. The anchor can include a suture-engaging member extending across the inner lumen, and the first suture can extend around the suture-engaging member. For another example, the anchor can include at least one suture-receiving groove formed in an external surface thereof and extending therealong such that, when the anchor is implanted in the bone, a suture positioned within the at least one suture-receiving groove can slide freely relative to the anchor.

In another embodiment, a suture anchor system is provided and includes an anchor having proximal and distal ends and being configured to be implanted in bone, a first suture coupled to the anchor, a second suture in the form of a continuous suture loop slidably disposed on the first suture, and an inserter tool having a handle portion and a separate tip portion. The tip portion can have a proximal end configured to removably mate to a distal end of the handle portion, and a distal end configured to removably mating the anchor to the tip portion of the inserter tool. When the tip portion and the anchor are mated, the tip portion and the anchor can be configured to be passed through the second suture.

In another aspect, a surgical method is provided for securing tissue to bone. In one embodiment, the method can include passing a suture anchor, with a distal tip portion of an inserter tool coupled thereto, through though a loop portion of at least one suture coupled to tissue, coupling the distal tip portion of the inserter tool to a handle portion of the inserter tool and manipulating the handle portion with the distal tip portion and the suture anchor attached thereto to implant the suture anchor in bone, and removing the proximal handle portion and the distal tip portion of the inserter tool from the suture anchor, leaving the suture anchor implanted in the bone.

In other aspects, a method is provided that includes passing a first suture through tissue such that a collapsible loop portion of the first suture extends from a first side of the tissue and first and second trailing ends of the first suture extend from a second opposite side of the tissue, the first and second trailing ends of the first suture being coupled to a suture anchor, and the collapsible loop portion of the first suture having a second suture in the form of a continuous loop disposed thereon. The method can further include passing the suture anchor, with a distal tip portion of an inserter tool coupled thereto, through the continuous loop, tensioning the first suture to slide the continuous loop along the collapsible loop portion of the first suture toward the tissue, and coupling the distal tip portion of the inserter tool to a handle portion of the inserter tool. The method can also include manipulating the handle portion with the distal tip portion and the suture anchor attached thereto to implant the suture anchor in bone, removing the proximal handle portion and the distal tip portion of the inserter tool from the suture anchor, leaving the suture anchor implanted in the bone, and tensioning the first suture relative to the suture anchor to thereby tension the collapsible loop portion of the first suture and to thereby tension the continuous loop relative to the tissue, thereby securing the tissue to the bone.

The method can vary in any number of ways. For example, tensioning the first suture to slide the continuous loop along the collapsible loop portion of the first suture toward the tissue can include pulling the suture anchor with the first suture coupled thereto. In another example, coupling the distal tip portion to the handle portion of the inserter tool can include coupling male and female mating elements on the distal tip portion and the handle portion of the inserter tool. In some embodiments, tensioning the first suture relative to the suture anchor can cause a slip knot formed on the first suture and disposed within the suture anchor to slide along the first suture to thereby tension the collapsible loop portion of the first suture and to thereby tension and lock the continuous loop relative to the tissue.

BRIEF DESCRIPTION OF THE DRAWINGS

The invention will be more fully understood from the following detailed description taken in conjunction with the accompanying drawings, in which.

DETAILED DESCRIPTION

Figure 1:
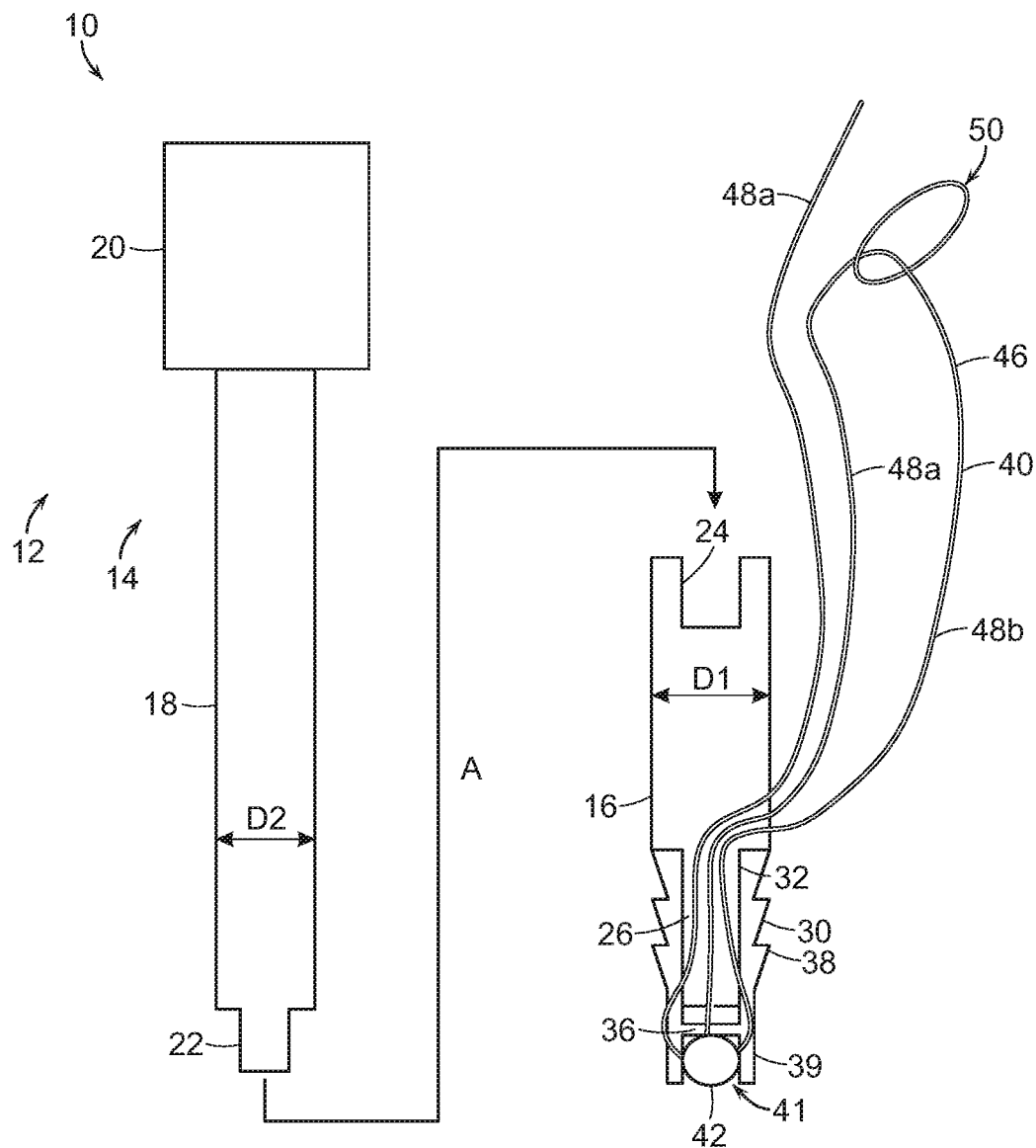
FIG. 1 is a side view of one embodiment of a suture anchor system including a two-piece inserter tool, a suture anchor, and first and second sutures.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various devices, systems, and methods are provided for securing soft tissue to bone. In general, various multi-piece inserter tools and methods of use are provided. In one exemplary embodiment, a two-piece inserter tool (also referred to herein as an "inserter") is provided having a tip portion configured to be removably and replaceably coupled to a handle portion of the inserter tool. The tip portion can have a size configured to allow the tip portion to be inserted into an inner lumen of a suture anchor (also referred to herein as an "anchor"). The anchor can have, or can be configured to have, one or more sutures coupled thereto. For non-limiting example, the anchor can be configured to be coupled to a first, adjustable suture and a second, continuous loop suture. The adjustable suture can include first and second trailing ends and a collapsible loop, and the continuous loop suture can be a continuous loop that is slidably disposed on the collapsible loop of the first suture. The tip portion of the inserter can have a size and shape that allows it to be passed through the continuous loop alone, as well as when the tip portion is coupled to the anchor. Because the handle portion can be coupled to the tip portion after the tip portion and the anchor have been passed through the continuous loop as a unit, the handle portion does not need to have a size that allows it to be passed through the continuous loop and can therefore have a larger size than the tip portion. The inserter tool can thus have a relatively large, easy-to-hold proximal handle while also having a distal tip that can couple to a suture anchor and pass through a relatively small suture loop. In using the anchor, the adjustable suture including the first and second trailing ends and the collapsible loop, and the continuous loop to secure soft tissue to bone, the collapsible loop is coupled to the continuous loop rather than being directly coupled to the soft tissue. The collapsible loop will thus not slide along the tissue during tensioning of the adjustable suture, e.g., as the collapsible loop collapses, and thus does not inadvertently cut, or "cheese wire," the soft tissue. The continuous loop also will not slide along the soft tissue when the soft tissue is pulled toward the bone.

FIG. 1 illustrates one exemplary embodiment of a suture anchor system 10 configured to anchor soft tissue to bone. The system 10 can include an inserter tool 12 and a suture anchor 30. The inserter tool 12 can be configured to deliver the suture anchor 30 to bone. A first, adjustable suture 40 can be configured to be slidably coupled to the anchor 30, and a second suture in the form of a continuous loop 50 can be configured to be slidably coupled to the adjustable suture 40.

The inserter tool 12 can be a multi-piece tool including at least two discrete portions configured to be removably and replaceably attached to one another. As in the illustrated embodiment, the inserter tool 12 can include two pieces, namely a handle portion 14 and a tip portion 16. As shown, the handle portion 14 can include an elongate shaft 18 having a handle 20 formed on a proximal end of the shaft 18. The handle 20 can facilitate grasping and manipulation of the tool 12. While in the illustrated embodiment, the inserter tool 12 includes two removably and replaceably coupled portions, in other embodiments, an inserter tool can include three or more removably and replaceably coupled portions. By way of non-limiting example, one or both of a tool's handle portion and tip portion can be multiple separable parts. For non-limiting example, an inserter's handle portion can include a handle and a separate shaft. The handle portion 14 can thus be chosen according to preferences of a user, e.g., left or right handed, small or large hands, different gripping features, different shaft diameters for differently sized access devices, patient anatomies, etc. For another non-limiting example, an inserter tool can have a plurality of differently sized and shaped distal tip portions that can allow the inserter to be used with differently sized anchors, and, as discussed below, differently sized continuous suture loops.

A distal end of the shaft 18 can include a first mating element 22 that can be configured to be removably coupled, as shown by arrow A, to a second mating element 24 formed on a proximal end of the tip portion 16. In the illustrated embodiment, the first and second mating elements 22, 24 are complementary male and female mating elements, respectively. The male and female mating elements 22, 24 can be configured to couple in various ways, such as via a threaded connection, snap-fit connection, interference fit, etc., as will be appreciated by a person skilled in the art. In another embodiment, a tip portion can have a male mating element that can be configured to removably couple to a female mating element on a handle portion.

The dimensions of the handle and tip portions 14, 16 of the insert tool 12 can vary. For non-limiting example, the tip portion 16 can have a first outer diameter D1, and the shaft 18 can have a second outer diameter D2. While the first outer diameter D1 of the tip portion 16 is shown as being substantially the same as the second outer diameter D2 of the shaft 18, the tip portion's outer diameter D1 can be less than or greater than the shaft's outer diameter D2. In an exemplary embodiment, the tip portion's outer diameter D1 is equal to or less than the outer diameter D2 of the shaft 18 because, as discussed more fully below, the tip portion 16 can be sized for passage through the continuous loop 50, whereas the shaft 18 and the handle 20 can be larger because they do not need to be passed through the continuous loop 50. The tip portion 16 and the handle portion 14 can each have any longitudinal length. As shown, the tip portion 16 can have a shorter longitudinal length than the handle portion 14. In other embodiments, a tip portion can have a longitudinal length that is equal to or greater than a longitudinal length of a handle portion. The longitudinal length of the tip portion 16 can be optimized so that, as discussed below, the tip portion 16 can be long enough easy grasping thereof, but short enough to facilitate passage of the tip portion 16 through the continuous loop 50. In an exemplary embodiment, the tip portion 16 can have a longitudinal length in a range of about 1 to 2 inches.

In certain embodiments, the tip portion 16 can include a reduced diameter portion 26 that is configured to fit within an inner lumen 32 of the anchor 30. A cross-sectional shape of the reduced diameter portion 26 can vary, but in an exemplary embodiment, the reduced diameter portion 26 can have a shape that allows the reduced diameter portion 26 to engage the inner lumen 32 extending through at least a proximal portion of the anchor 30. The reduced diameter portion 26 can be a male mating element configured to be received in a corresponding female element of the anchor 30, e.g., in the inner lumen 32. In the illustrated embodiment, the reduced diameter portion 26 has a generally circular cross-sectional shape that complements the generally circular cross-sectional shape of the inner lumen 32 in the anchor 30. In another embodiment, an inner lumen of the anchor can have another cross-sectional shape, such as a generally hexagonal cross-sectional shape that can complement a generally hexagonal cross-sectional shape of an inner lumen extending through at least a proximal portion of an anchor.

A longitudinal length of the reduced diameter portion 26 can vary, but in an exemplary embodiment, the reduced diameter portion 26 can have a longitudinal length that allows the reduced diameter portion 26 to extend through a substantial portion of the anchor's lumen 32. For non-limiting example, the longitudinal length of the reduced diameter portion 26 can allow the reduced diameter portion 26 to extend through the inner lumen 32 to a point just proximal of a suture-engaging member 36 positioned in a distal portion of the anchor 30. The suture-engaging member 36 is discussed further below. A person skilled in the art will appreciate that the reduced diameter portion 26 can have a variety of shapes, sizes, and configurations so that the reduced diameter portion 26 can be configured to be disposed within anchors of various shapes, sizes, and configurations.

The tip portion 16 can be configured to receive multiple strands of the adjustable suture 40. The tip portion 16 can be configured to allow the adjustable suture 40 to be coupled to the anchor 30, and to allow multiple strands of the adjustable suture 40 to be passed through the tip portion 16 so as to extend proximally beyond the anchor 30 and the tip portion 16. For non-limiting example, the tip portion 16 can have one or more inner lumens extending therethrough and/or one or more suture-seating features, e.g., recesses, grooves, etc., formed in an external surface thereof configured to receive one or more sutures therein. The one or more suture-seating features can allow suture(s) seated therein to be seated flush or sub-flush with the external surface of the tip portion 16. This seating can facilitate free slidable movement of the suture(s) relative to the top portion 16.

Figure 2:
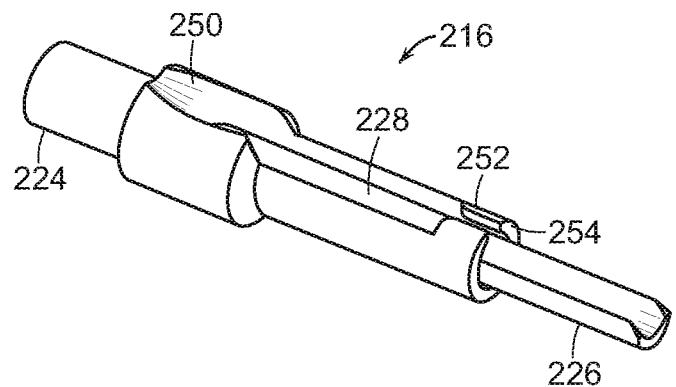
FIG. 2 is a perspective view of an embodiment of a tip portion of an inserter tool.
Figure 3:
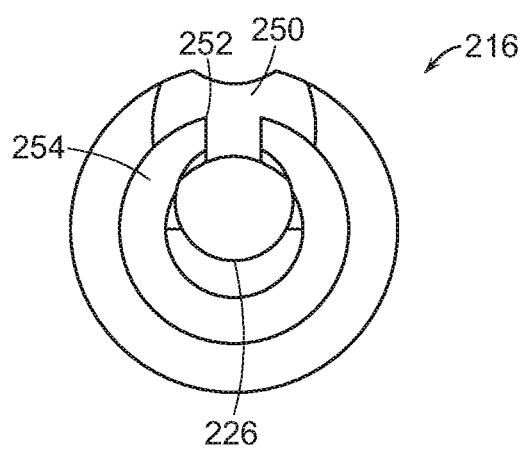
FIG. 3 is an end view of the tip portion of FIG. 2.

FIGS. 2-3 illustrate an embodiment of a tip portion 216 that includes a suture-seating groove 228. While a tip portion can have any number of suture grooves, the illustrated tip portion 216 has a single groove 228 that extends longitudinally from a distal end of the tip portion 216 and terminates distal of a proximal end of the tip portion 216. In other embodiments, a suture receiving groove can extend another distance along an axial length of a tip portion, including along an entire longitudinal length of the tip portion. A proximal portion of the groove 228 can include an angled portion 250, which can provide a smooth transition between an external surface of the tip portion 216 and the groove 228. The angled portion 250 can thus help reduce wear on a suture seated in the groove 228. The groove 228 can include a reduced-area portion 252 in which an open width of the groove 228 is decreased, thereby forming a partially-enclosed groove. This decreased open width can help prevent anchor breakage when impacted into bone, and it can also help aid in retaining a suture within the groove 228. In other embodiments, the groove can be entirely enclosed and in the form of a tunnel.

Figure 4:
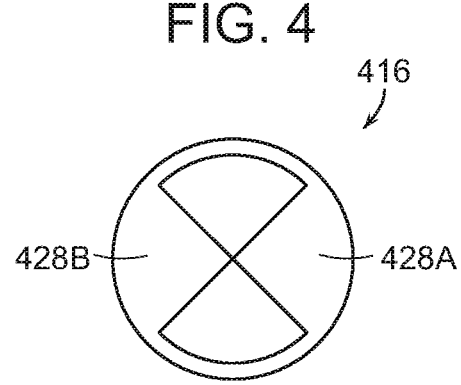
FIG. 4 is an end view of another embodiment of a tip portion of an inserter tool.

A tip portion having multiple suture seating features can be sized to seat one or more suture strands. Having multiple suture seating features can facilitate an ordered arrangement of multiple suture strands. FIG. 4 illustrates an exemplary embodiment of a tip portion 416 having multiple suture seating features in the form of grooves 428A, 428B. The grooves 428A, 428B can have any size, configuration, and shape. Although only two grooves 428A, 428B are shown, as mentioned above, a tip portion can include more than two suture seating features, In the illustrated embodiment, the grooves 428A, 428B have a substantially triangular cross sectional shape, are substantially the same size, and are on opposed sides of the tip portion 416. The substantially triangular shape can facilitate retention of one or more sutures in the grooves 428A, 428B, e.g., in a pointed portion of the grooves 428A, 428B toward a radial center of the tip portion 416. In some embodiments, the suture seating features can have different sizes for, e.g., retention of different numbers or sizes of strands of suture; the suture seating features can be at a position other than on opposed sides of a tip portion; e.g., spaced ninety degrees apart; and the suture seating features can have a rounded cross sectional shape, etc.

Similar to the tip portion 16 of FIG. 1, the tip portion 216 shown in FIG. 2 can include a mating element 224 configured to removably couple the tip portion 216 to the handle portion 16 and/or one or more other handle portions. The tip portion 216 can include at a distal end thereof a reduced diameter portion 226 configured to be inserted into an inner lumen of the anchor. A shoulder 254 at a proximal end of the reduced diameter portion 226 can be configured to abut a proximal end of an anchor when the reduced diameter portion 226 is inserted into the anchor's inner lumen. The shoulder 254 can transfer a driving force from a proximal portion of an inserter tool to the anchor, and can prevent a distal end of the reduced diameter portion 226 from coming into contact with a suture-engaging member in the anchor and/or sutures coupled to the anchor to thereby prevent the reduced diameter portion 226 from damaging sutures disposed around the suture-engaging member, or otherwise damaging the sutures. The shoulder 254 can also provide an indication to a user that the tip portion 216 is fully inserted in an anchor because the shoulder 254 abutting the proximal end of the anchor can be palpably felt when the reduced diameter portion 226 of the tip portion 216 is advanced distally into the anchor's inner lumen.

Referring again to FIG. 1, the anchor 30 can have a variety of shapes, sizes, and configurations. Various exemplary embodiments of suture anchors that can be used with the inserters disclosed herein are described in further detail in U.S. Pat. No. 8,114,128 entitled "Cannulated Suture Anchor" issued Feb. 14, 2012, U.S. Patent Publication No. 2009/0076544 entitled "Dual Thread Cannulated Suture Anchor" filed Sep. 14, 2007, U.S. Patent Application No. 2012/0165864 entitled "Adjustable Anchor Systems and Methods" filed Dec. 23, 2010, and U.S. patent application Ser. No. 13/331,867 entitled "Knotless Instability Anchor" filed Dec. 20, 2011, which are hereby incorporated by reference in their entireties. Non-limiting examples of suture anchors that can be used with the inserters disclosed herein include GRYPHON™ Anchors and HEALIX™ Anchors available from Depuy Mitek, Inc. of Raynham, Mass. The suture anchors discussed herein can have any of a variety of sizes, depending on patient anatomy, procedure type, suture size, and/or various other parameters, which will be appreciated by a person skilled in the art. In some embodiments, the suture anchors discussed can have a size in a range between about 1 mm to 12 mm in diameter and in a range between about 2 mm to 24 mm in length.

In the illustrated embodiment, the anchor 30 includes an elongate member having proximal and distal ends with the inner lumen 32 extending between the proximal and distal ends of the anchor 30. As discussed above, the inner lumen 32 can be configured to receive at least a portion of the tip portion 16 therein, e.g., the reduced diameter portion 26 of the tip portion 16. The lumen 32 can extend through an entire length of the anchor 30 from a proximal end of the anchor 30 to the distal end of the anchor 30, as in the illustrated embodiment, or the inner lumen 32 can extend from the proximal end of the anchor 30 to a point proximal of the distal end of the anchor 30.

As mentioned above, the anchor 30 can include the suture-engaging member 36 formed therein. The suture-engaging member 36 can have a variety of sizes, shapes, and configurations. An angular orientation of the suture-engaging member 36 relative to a longitudinal axis of the inner lumen 32 can vary, but in an exemplary embodiment the suture-engaging member 36 extends substantially perpendicular to a longitudinal axis of the inner lumen 32. A location of the suture-engaging member 36 can also vary, but in an exemplary embodiment the suture-engaging member 36 is positioned at or adjacent to a distal end of the suture anchor 30. In the embodiment shown in FIG. 1, the suture-engaging member 36 is located just proximal to a distal-most end of the suture anchor 30 so as to form a suture-seating groove 41 in the distal-most end of the suture anchor 30. This recessed configuration of the suture-engaging member 36 can allow suture(s) disposed around the suture-engaging member 36 to sit flush or sub-flush with the distal end of the suture anchor 30, which can help prevent the suture(s) from interfering with insertion of the suture anchor 300 into bone. A knot 42 formed in the adjustable suture 40 is shown in FIG. 1 seated in the suture-seating groove 41. A person skilled in the art will appreciate that the suture-engaging member 36 can be integrally formed with the suture anchor 300, e.g., the suture anchor 30 and suture-engaging member 36 can be molded as a single unit or formed from a single piece of material, or the suture-engaging member 36 can be an independent element fixedly or removably mated to the suture anchor 30.

The suture-engaging member 36 can be configured to engage one or more sutures that extend through the inner lumen 32 of the suture anchor 30. As in the illustrated embodiment, the suture-engaging member 36 can be configured to prevent the knot 42 of the adjustable suture 40 from moving in a proximal direction when proximal tension is applied to the adjustable suture 40, as discussed further below. The distal end of the anchor 30 can include a pointed or rounded tip 39, which can facilitate insertion of the anchor 30 into bone.

The anchor 30 can include at least one bone-engaging surface feature 38 configured to engage bone. The at least one bone-engaging surface feature 38 can have a variety of configurations, shapes, and sizes. The at least one bone-engaging surface feature 38 can be formed on at least a portion of an external surface of the anchor 30, e.g., in a proximal portion of the anchor 30. A distal portion of the anchor 30 can be free of the at least one bone-engaging surface feature 38, which can facilitate insertion of the anchor 30 into bone. In another embodiment, at least one bone-engaging surface feature can be formed along an entire length or along discrete portions of an anchor. While various bone-engaging surface features can be used, such as teeth, ridges, flanges, ribs, barbs, protrusions, etc., as in the illustrated exemplary embodiment, the anchor 30 can include at least one bone-engaging surface feature 38 in the form of one or more ridges. In the illustrated embodiment, the anchor 30 includes a plurality of ridges spaced axially along a length of the proximal portion of the anchor 30.

An anchor can include one or more suture-receiving grooves (not shown) formed on an external surface of the anchor, similar to the grooves 428A, 428B in the tip portion 416 of FIG. 4. The groove(s) can extend therealong the anchor such that, when the suture anchor is implanted in bone, suture(s) positioned within the groove(s) can slide freely relative to the anchor. The groove(s) can extend along any portion of the anchor, but in an exemplary embodiment, the groove(s) can extend at least from a proximal end of the anchor to a suture-engaging member in a distal portion of the anchor, which can allow suture(s) extending around the suture-engaging member to be seated in the groove(s).

Figure 5:
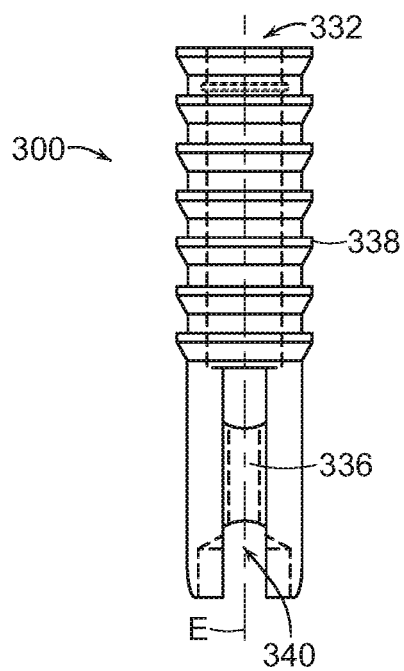
FIG. 5 is a side, partially transparent view of another embodiment of a suture anchor.
Figure 6:
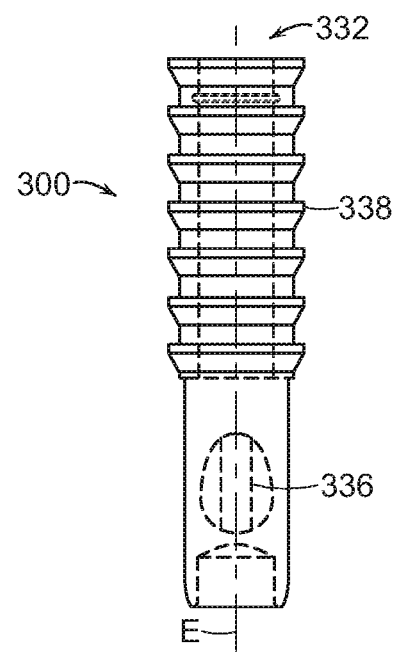
FIG. 6 is another side, partially transparent view of the anchor of FIG. 5.
Figure 7:
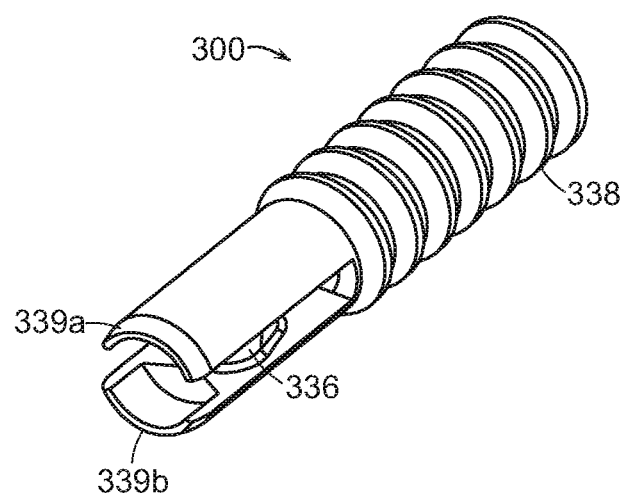
FIG. 7 is a perspective view of the anchor of FIG. 5.

FIGS. 5-7 illustrate another embodiment of an anchor 300. The anchor 300 in the illustrated embodiment includes a suture-engaging member 336 in the form of a post that extends transversely across an inner lumen 332 of the anchor 300 and between opposed inner sidewalls of the suture anchor 300. An angular orientation of the suture-engaging member 336 relative to a longitudinal axis E of the inner lumen 332 can vary, as mentioned above regarding the suture-engaging member 36 of FIG. 1. The anchor 300 can include a plurality of bone-engaging surface features 338, which in the illustrated embodiment are in the form of a plurality of circumferential ridges spaced axially along a proximal portion of the anchor 300 that terminate at a location proximal to the suture-engaging member 336. The anchor 300 can also include one or more bone-penetrating features 339a, 339b at the distal-most end thereof that are configured to facilitate insertion of the anchor 300 into bone. The bone-penetrating features 339a, 339b in the illustrated embodiment include a chamfered edge and pointed tip. The space between the opposed bone-penetrating features 339a, 339b can define a pocket for seating a knot in a suture, as will be discussed below.

The suture anchors discussed herein can be formed from any one or more of a variety of materials. In some embodiments, the suture anchors can be formed from a biocompatible, bioabsorbable material which can reduce immunological problems associated with having a foreign substance within the body over a prolonged period of time. Exemplary materials from which the suture anchors discussed herein can be formed include bioabsorbable elastomers, copolymer combinations such as polylactic acid-polyglycolic acid (PLA-PGA), and bioabsorbable polymers such as aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (e.g., biopolymers such as collagen, elastin, bioabsorbable starches, etc.) and blends thereof. In some embodiments, the suture anchors can be formed from polylactic acid, or a composite blend of tricalcium phosphate and polylactic acid. The suture anchors discussed herein can also be formed from non-absorbable materials, such as polyether ether ketone (PEEK), polysulfone, or metals such as titanium. A suture-engaging element of the suture anchor can also be formed from any one or more of the materials listed above, including titanium.

Referring again to FIG. 1, the anchor 30 can be configured to couple to one or more sutures, e.g., the adjustable suture 40 and the continuous loop 50. While only two sutures 40, 50 are illustrated in FIG. 1, any number of sutures can be coupled to the anchor 30 and used to secure soft tissue to bone. The adjustable suture 40 and the continuous loop 50 can be made from the same or different material and can have the same or different diameters. For non-limiting example, one of the sutures 40, 50 can be formed from a suture having a lower abrasive property at its surface. The lower abrasive property can be achieved by a larger diameter, a softer composition, a softer braid, plait or strand pattern, or a combination of such characteristics. The continuous loop 50 can be formed from a suture that is tied with a fixed knot to form the continuous loop, or alternatively, the continuous loop 50 can be molded or otherwise formed as a ring of material. The diameter of the continuous loop 50 can vary depending on the surgical procedure and the anatomy of the patient. The diameter of the continuous loop 50 can be sized so that, as discussed more fully below, the continuous loop 50 is small enough to sufficiently engage tissue to be approximated, and not be pulled into the inner lumen 32 of the anchor 30, but large enough that the anchor 30 and the tip portion 16 can be passed through the continuous loop 50 and large enough to substantially wrap around the soft tissue (see FIG. 11). In some embodiments, the diameter of the continuous loop 50 can be in a range of about 2 mm to 50 mm, and in other embodiments be less than 25 mm, 15 mm, 10 mm, or 5 mm, etc. The adjustable suture 40 and the continuous loop 50 can be coupled to the anchor 30 in a variety of ways, e.g., by hand, by using a suture threading device, etc. In some embodiments, the adjustable suture 40 can be pre-coupled to the continuous loop 50 and can be pre-loaded within the inner lumen 32 of the anchor 30, e.g., packaged as a pre-loaded unit, which can speed usage of the anchor 30 in a surgical procedure.

As shown in FIG. 1, the adjustable suture 40 can be in the form of a single elongate strand that is folded, e.g., folded in half, to form a collapsible loop 46 having first and second trailing ends 48a, 48b. One of the first and second trailing ends 48a, 48b, e.g., the second trailing end 48b, can be tied into a slip knot 42 slidably disposed along the other trailing end, e.g., the first trailing end 48a, such that the first trailing end 48a extends from the knot 42. As a result, a portion of the collapsible loop 46 extending from one side of the knot 42 is referred to herein as a collapsible loop portion, and a portion extending from the other side of the knot 42 is referred to herein as a first free end. The continuous loop 50 can be a continuous, closed loop slidably disposed on the collapsible loop 46 of the adjustable suture 40. The knot 42 can be any sliding and/or lockable knot, as will be appreciated by a person skilled in the art, such as a Tennessee Slider knot. Various embodiments of knots are described further in previously mentioned U.S. Patent Application No. 2012/0165864. While the adjustable suture 40 in the illustrated embodiment includes only a single knot 42, the adjustable suture 40 can include any number of knots as appropriate for a certain procedure or as preferred by a surgeon. While the adjustable suture 40 in the illustrated embodiment only has one free end and the collapsible loop portion via a single knot 42, any other configuration where tension on one or more free ends of a suture results in slidably pulling a continuous loop towards a suture anchor can be used. For non-limiting example, a suture anchor can be configured to allow one or more sutures to be so configured without the need for a sliding knot. In one embodiment, a suture anchor can have a locking element or feature that can be configured to lock a suture relative to the anchor without the need for a knot. In other aspects, trailing ends of a suture extending from a suture anchor can be tied off.

A suture anchor kit can be provided including one or more anchors, two or more sutures, and one or more inserter tools, including any number of handle portions and/or tip portions, each configured to removably and replaceably mate with at least one of the anchors. Alternatively, the kit can include one or more anchors and one or more inserter tool tip portions, and the sutures can be separately obtained. In an exemplary embodiment, each of the tip portions in a kit can have a different size, e.g., a different outer diameter, and can be configured to removably couple to an inserter handle portion. The inserter handle portion can be included in the kit and can be configured to removably and replaceably mate with each of the tip portions in the kit. Each of the sutures can have different material properties or thicknesses. At least one of the sutures in the kit can be in the form of a continuous loop. The continuous loop(s) can have different circumferences. Each of the anchors can have different sizes and/or different configurations for engaging bone. In this way, the anchors, sutures, and tip portions having the most appropriate sizes, shapes, and configurations can be selected for use in a particular surgical procedure with a particular patient, which can help a single kit accommodate different situations, such as different surgical procedures, different patient anatomies, and various tissue sizes. As discussed below, the suture(s) can be pre-loaded in the anchors(s), or the suture(s) can be loaded during surgery.

FIGS. 8-15 illustrate an exemplary embodiment of a surgical procedure for soft tissue repair. Although the procedure is illustrated with respect to the inserter tool 12 and the anchor 30 of FIG. 1, any of the anchors and inserter tools discussed herein can be similarly used. In the illustrated embodiment, the soft tissue repair is performed via a minimally invasive procedure, such as an arthroscopic procedure where one or more access devices are used to form working channels from outside of a patient's body to a surgical site. For ease and clarity of illustration, the one or more access devices are not illustrated in FIGS. 8-15. In addition, the illustrated embodiment is not limited to minimally invasive procedures and can, for non-limiting example, be performed in open surgery or in robot-assisted surgery. Also, although the procedure is illustrated with respect to a soft tissue repair, any of the suture anchors and inserter tools discussed herein can be used to surgically repair various problems.

Figure 8:
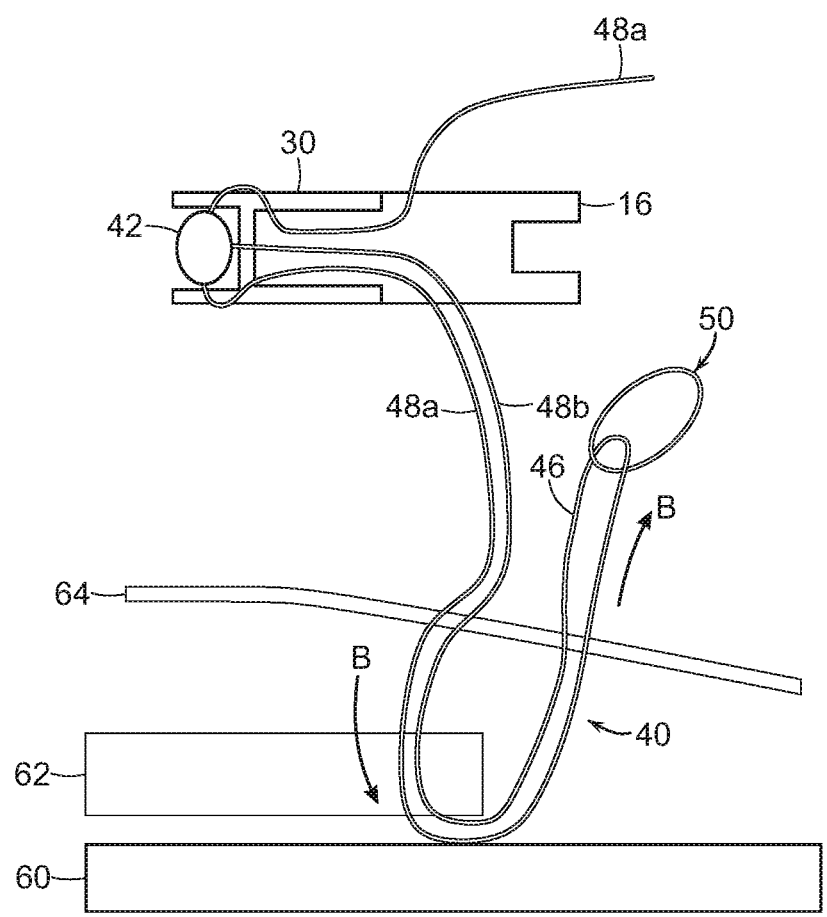
FIG. 8 is a side cross-sectional, schematic view of the first and second sutures of FIG. 1 passed through a tissue and coupled to the anchor of FIG. 1 and the tip portion of the inserter tool of FIG. 1.

As shown in FIG. 8, an incision in skin 64 can be formed in proximity to an area of a bone 60 of a patient to which a piece of soft tissue 62 is to be approximated. The adjustable suture 40 and the continuous loop 50 can then be passed through the incision, e.g., using a minimally-invasive surgical access device (not shown). The adjustable suture 40 and the continuous loop 50 can be passed through the soft tissue 62 in a direction of arrow B, e.g., using a needle (not shown), so that the continuous loop 50 and the collapsible loop portion 46 of the adjustable suture 40 can extend from one side of the tissue 62, and the first and second trailing ends 48a, 48b of the adjustable suture 40 can extend from another, opposite side of the tissue 62. The direction of the arrow B is an illustrative example only, and depending on an orientation of the tissue 62, other patient anatomy, and/or on surgeon preference, the adjustable suture 40 and the continuous loop 50 can be passed in another direction. After passing the adjustable suture 40 and the continuous loop 50 through the tissue 62, the continuous loop 50 with the collapsible loop 46 coupled thereto can be pulled back through the access device and the incision so that the continuous loop 50 is positioned outside the patient's body, as illustrated in FIG. 8.

The anchor 30 and the tip portion 16 can be coupled to the adjustable suture 40 before the adjustable suture 40 and the continuous loop 50 are passed through the tissue 62, as shown in FIG. 8. Alternatively, the anchor 30 and the tip portion 16 can be coupled to the adjustable suture 40 after the adjustable suture 40 and the continuous loop 50 have been passed through the tissue 62.

Depending on a surgical procedure being performed, a circumference of the continuous loop 50 can be relatively small, e.g., in a range of about 2 mm to 50 mm. Passing the anchor 30 through the continuous loop 50 can therefore be challenging. To make passing the anchor 30 through the continuous loop 50 easier, the tip portion 16 of the inserter tool 12 can be coupled to the anchor 30 prior to the anchor 30 being passed through the continuous loop 50 to allow the anchor 30 and the tip portion 16 to be advanced through the continuous loop 50 as a single unit. In the illustrated embodiment, the tip portion 16 is coupled to the anchor 30 before the anchor 30 is passed through the continuous loop 50. Further, a typical suture anchor is a relatively small device, e.g., in a range of about 1 mm to 12 mm in diameter and in a range of about 2 mm to 24 mm in length, which can make the anchor difficult to grasp. For example, it can be difficult to mount the anchor on the tip while managing the sutures coupled to the anchor. If the sutures get pinched or twisted around each other during assembly, then the sutures will not slide smoothly and the sliding knot may not work properly. Therefore, it is preferred to have the suture, anchor, and tip assembled during manufacture. As discussed above, in the illustrated embodiment, the tip portion 16 can have a length in a range of about 1 to 2 inches. Thus, the relatively large tip portion 16 can allow the relatively small anchor 30 to be more easily grasped, e.g., by hand, by tool, by robotic arm, etc., making passage of the anchor 30, and any sutures coupled thereto, through the continuous loop 50 easier.

Because the tip portion 16 can be separable from the handle portion 14, an entirety of the inserter tool 12 need not be advanced through the continuous loop 50. Instead, only a relatively small portion of the inserter tool 12 need be advanced through the continuous loop 50, namely the tip portion 16, to couple the anchor 30 to a driver device. The anchor 30 can thus be passed through the continuous loop 50 without having to spend time feeding a relatively lengthy driver device through the continuous loop 50, which could risk fraying or otherwise damaging the suture and having to begin the suture coupling process all over again. The handle portion 14 can be configured to couple to the tip portion 16 after the tip portion 16 and the anchor 30 have been passed through the continuous loop 50, thereby avoiding passage of the relatively lengthy handle portion 14 through the continuous loop 50 while facilitating handling of the anchor 30 from outside the patient's body. Having two or more inserter tool portions can therefore allow the inserter 12 to have a first, relatively narrow tip portion 16 of, e.g., the tip portion 16 having the first diameter D1, and a second, larger portion, e.g., the handle portion 14 having the second diameter D2, which can be more easily handled by hand and/or instrument than the smaller tip portion 16.

Figure 9:
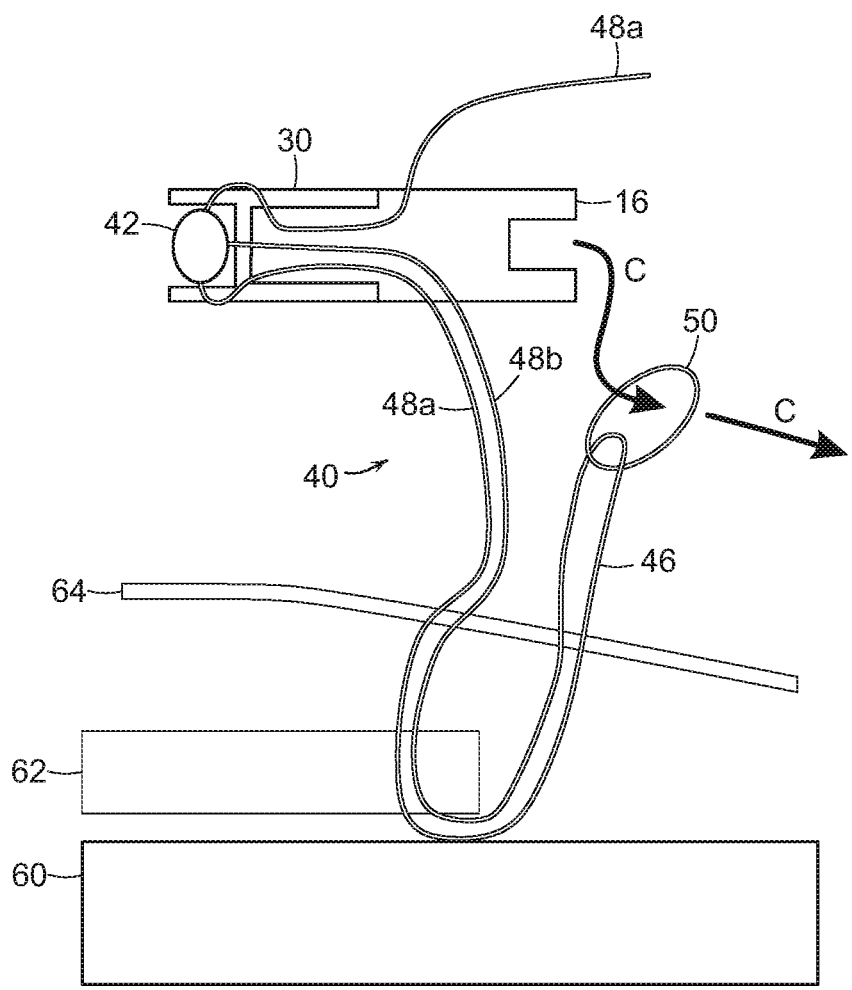
FIG. 9 is a side cross-sectional, schematic view showing the tip portion and the anchor of FIG. 6 about to be passed through a continuous loop of the second suture of FIG. 8.

As shown in FIG. 9, after the adjustable suture 40 and the continuous loop 50 have been passed through the tissue 62 and the continuous loop 50 is positioned outside of the patient's body, the tip portion 16 and the anchor 30 can be passed through the continuous loop 50, as shown by arrow C. The direction of the arrow C is an illustrative example only, and depending on an orientation of the tip 16, the anchor 30, the continuous loop 50, etc. and/or on surgeon preference, the tip 16 and the anchor 30 can be passed in another direction through the continuous loop 50. As shown, the proximal end of the tip portion 16 can be passed through the continuous loop 50 first. Alternatively, the distal end of the anchor 30 can be passed through the continuous loop 50 first. Passing the proximal end of the tip portion 16, and hence the proximal end of the anchor 30, through the continuous loop 50 first can help position the distal end of the anchor 30 in a more natural position for advancement through the skin 64 and into the bone 60 underlying the skin 64.

Figure 10:
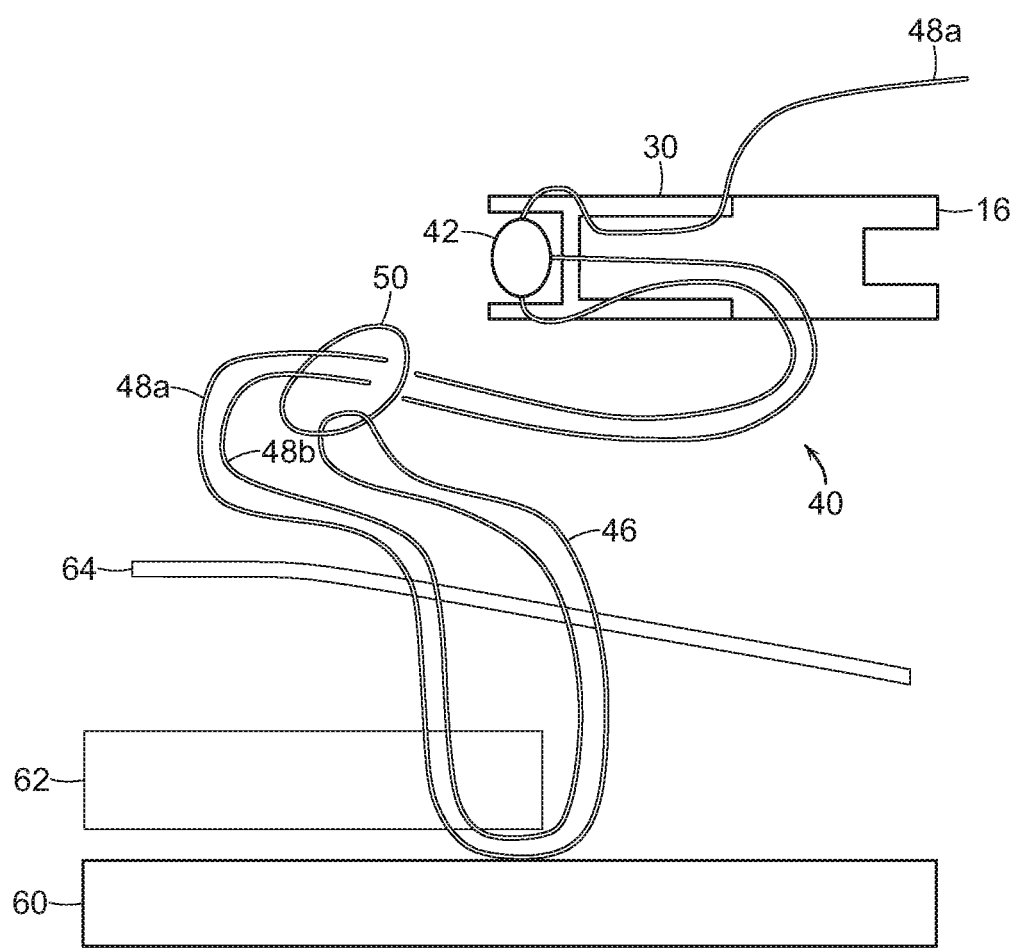
FIG. 10 is a side cross-sectional, schematic view of the tip portion and the anchor of FIG. 7 passed through the continuous loop of the second suture of FIG. 9.
Figure 11:
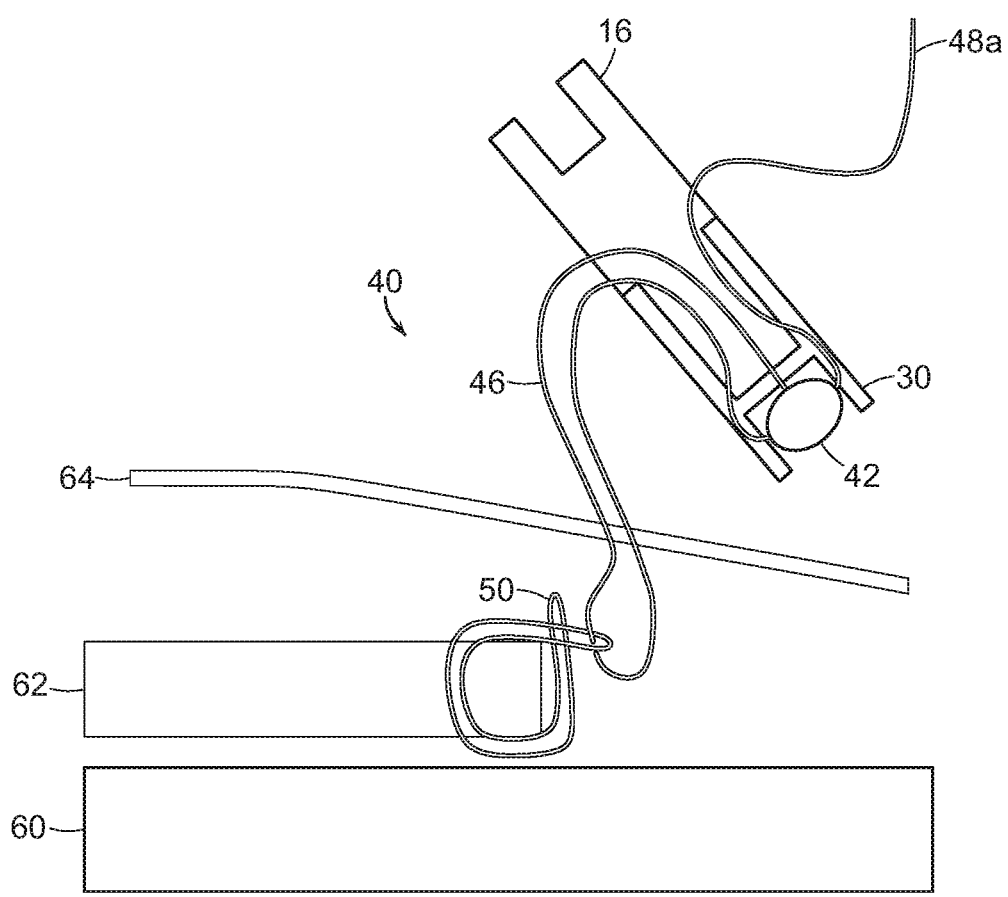
FIG. 11 is a side cross-sectional, schematic view of the second suture of FIG. 10 slid down the first suture to be positioned around the tissue.

As shown in FIG. 10, with the anchor 30 and the tip portion 16 positioned outside the patient's body and passed through the continuous loop 50 such that the continuous loop 50 is slidably disposed along the collapsible loop 46 of the adjustable suture 40. Proximal tension can be applied to the adjustable suture 40, thereby sliding or "zip lining" the continuous loop 50 along the collapsible loop 46, e.g., along the collapsible loop portion 48b. This sliding or "zip lining" can pull the continuous loop 50 through the access device (not shown), into the patient's body through the skin 64, and around the tissue 62, as shown in FIG. 11. A length of the collapsible loop portion of the adjustable suture 40 can be adjusted by applying proximal tension to the free end 48a of the adjustable suture 40, which can help eliminate any unnecessary excess length or slack in the collapsible loop 46 of the adjustable suture 40.

Figure 12:
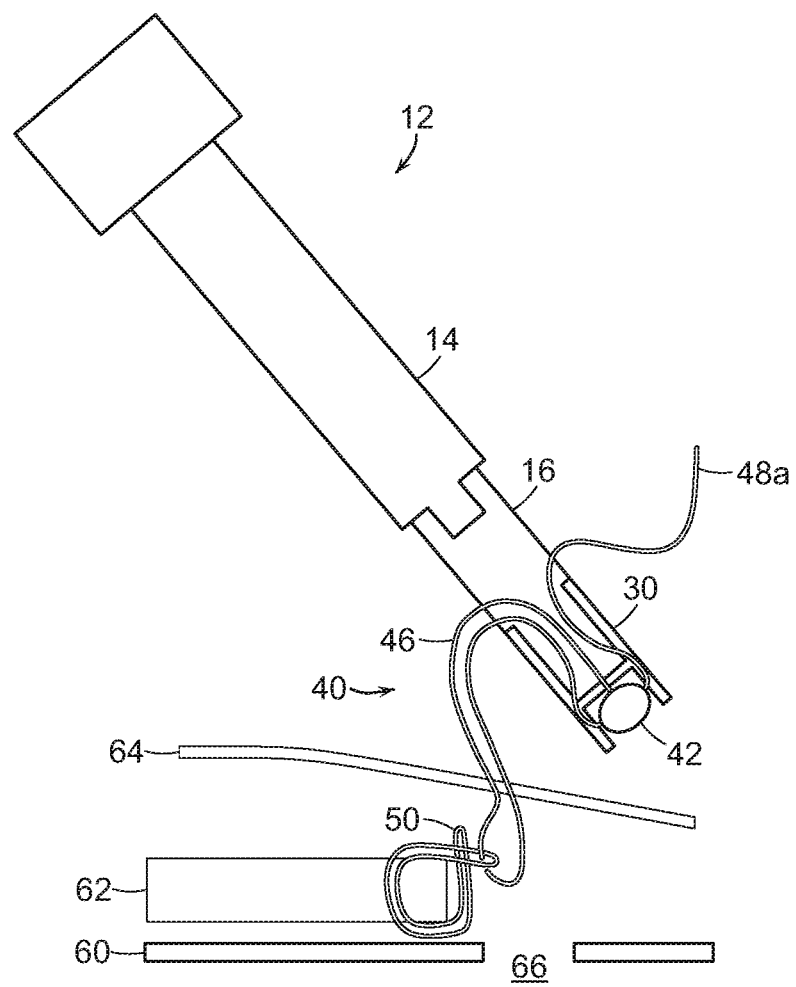
FIG. 12 is a side cross-sectional, schematic view of the tip portion of FIG. 10 coupled to a handle portion of the inserter tool of FIG. 1.

As shown in FIG. 12, with the continuous loop 50 extending through the tissue 62 and being slidably disposed on the collapsible loop 46, the handle portion 14 of the inserter tool 12 can be coupled to the tip portion 16, e.g., by mating the first and second complementary male and female mating elements 22, 24. The handle and tip portions 14, 16 can, however, be mated together prior to tensioning the adjustable loop 46. As shown in FIG. 12, if not previously formed, a hole 66 can be formed in the bone 60, e.g., drilled in the bone 60. Alternatively, the suture anchor 30 can be self-drilled or self-tapped directly into the bone 60 such that the hole 66 is not pre-formed.

Figure 13:
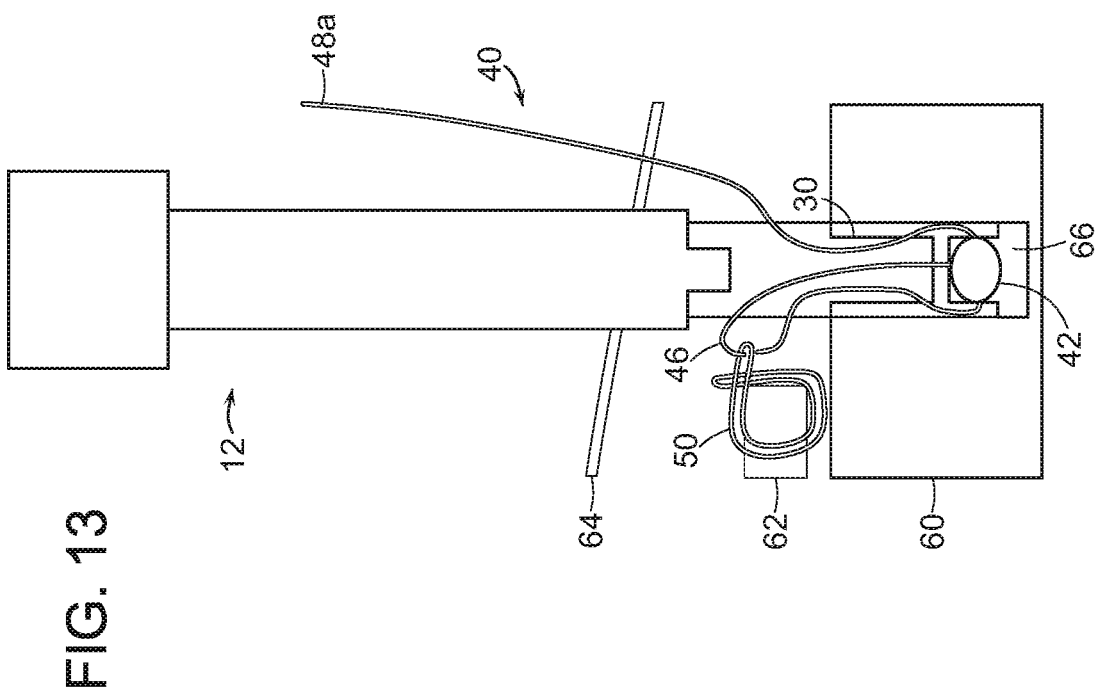
FIG. 13 is a side cross-sectional, schematic view of the tip portion and the anchor of FIG. 12 positioned in a bone hole.

The inserter tool 12 can be used to advance the anchor 30 into the bone 60, as shown in FIG. 13. During insertion of the anchor 30 into the bone 60, the free end 48a of the adjustable suture 40 can be positioned external to the inserter tool 12 and proximal of the incision. In some embodiments, a handle portion of an inserter tool can be cannulated such that a free end of a first suture can extend through the handle portion and out a proximal end thereof.

Figure 14:
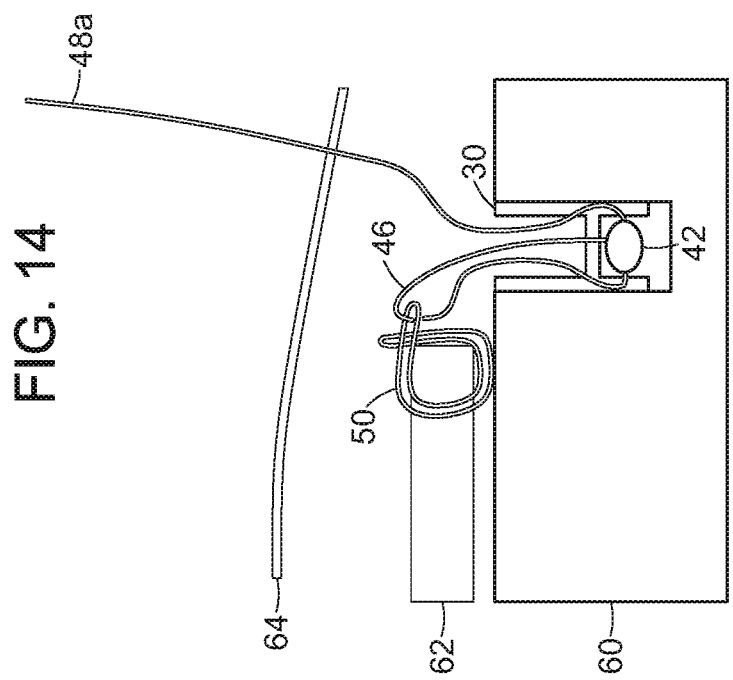
FIG. 14 is a side cross-sectional, schematic view of the anchor of FIG. 13 with the entire inserter tool removed therefrom.
Figure 15:
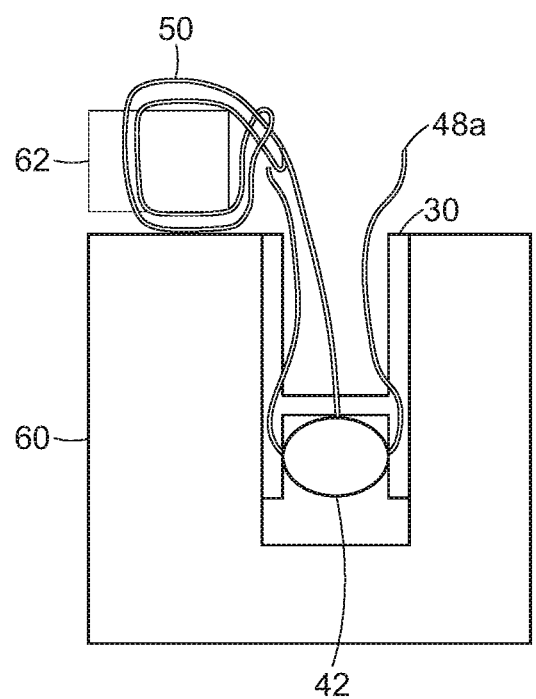
FIG. 15 is a side cross-sectional, schematic view of the anchor of FIG. 14 with the first and second sutures tightened and an excess of the first suture trimmed and removed.

As illustrated in FIG. 14, a proximal tension can be applied to the free end 48 of the adjustable suture 40, thereby collapsing the collapsible loop 46 by sliding the knot 42 therealong. This can be done either before or after removing the inserter, but preferably after removing the inserter. As the collapsible loop 46 collapses, the collapsible loop 46 slides along the continuous loop 50 and applies a pulling force to the continuous loop 50, which pulls the continuous loop 50 and the tissue 62 towards the bone 60, as shown in FIG. 15. Because the collapsible loop 46 external to the tissue 62 and sliding relative to the continuous loop 50 extending through the tissue 62, which merely tightens, positioning the tissue 62 against the bone 60 can involve a minimal amount of suture sliding through the tissue 62, thereby reducing chances of tissue damage, e.g., by reducing chances of cheese-wiring through the tissue 62. In the illustrated embodiment, the diameter of the continuous loop 50 is sized for use with multiple tissue thicknesses. For example, the continuous loop 50 can have a diameter that allows the loop to extend into the inner lumen 32 of the anchor 30, thus ensuring that the loop will retain any tissue thickness and essentially providing a one-size-fits-all suture anchor system. While the loop 50 can extend into the inner lumen 32 of the anchor 30, the loop 50 preferably does not extend all the way to the suture-engaging member 36. The adjustable suture 40 can be secured if, for example, the knot 42 and/or the suture-engaging member 36 does not automatically lock the adjustable suture 40 in place.

After advancing the anchor 30 into the bone 60 and tensioning the adjustable suture 40 to secure the tissue 62 to the bone 60, the inserter tool 12 can be removed from the anchor 30 as a single unit, e.g., with the handle and tip portions 14, 16 attached together. Removing the tool 12 as a single unit can facilitate removal of the relatively small tip 16 from the anchor 30 positioned in the bone 60. Any excess amount of the adjustable suture 40 can be trimmed and removed. In an exemplary embodiment, the inserter is removed before tensioning the tissue. This can provide the surgeon with an unobstructed view and freedom from the inserter.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on anatomy of a subject in which the devices will be used, size and shape of components (e.g., sutures) with which the devices will be used, and the methods and procedures in which the devices will be used. The figures provided herein are not necessarily to scale. Although the devices and methods disclosed herein are generally directed to surgical techniques, they can also be used in applications outside of the surgical field.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. An inserter tool comprising:
   a handle having an elongate shaft extending distally therefrom; and
   a tip portion having a proximal end configured to removably mate to a distal end of the elongate shaft, and a distal end configured to removably mate to a suture anchor, the distal end of the tip portion including a reduced diameter portion that is configured to be inserted into the suture anchor, the tip portion including a groove extending longitudinally from the distal end of the tip portion, and the groove being partially enclosed by a shoulder that is configured to abut against a proximal end of the suture anchor with the reduced diameter portion inserted into an inner lumen of the suture anchor, wherein the proximal end of the tip portion and the distal end of the elongate shaft include complementary male and female mating elements configured to mate the tip portion to the elongate shaft.

2. The inserter tool of claim 1, wherein the reduced diameter portion has a cross-sectional shape configured to complement a cross-sectional shape of an inner lumen of the suture anchor.

3. The inserter tool of claim 1, wherein the shoulder is configured to transfer a driving force from the handle to the suture anchor.

4. The inserter tool of claim 1, wherein a proximal portion of the groove includes a first sloped portion that connects a second portion of the groove to an external portion of the tip portion.

5. The inserter tool of claim 1, wherein the groove has a width that varies along a length of the groove.

6. The inserter tool of claim 1, wherein the proximal end of the tip portion and the distal end of the elongate shaft include threads formed thereon and configured to threadably mate to one another.

7. The inserter tool of claim 1, wherein the proximal end of the tip portion and the distal end of the elongate shaft have a snap-fit connection for mating to one another.

8. The inserter tool of claim 1, wherein the handle is cannulated.

9. A suture anchor system comprising:
   a suture anchor having proximal and distal ends, the suture anchor being configured to be implanted in bone, and the suture anchor having a suture-seating groove at the distal end thereof; and
   an inserter tool having a handle portion and a tip portion, the handle portion having an elongate shaft extending distally therefrom, the tip portion having a proximal end configured to removably mate to a distal end of the handle portion and a distal end configured to removably mate to the suture anchor, the distal end of the tip portion including a reduced diameter portion that is configured to be inserted into the anchor, the tip portion including a groove extending longitudinally from the distal end of the tip portion, and the groove being partially enclosed by a shoulder that is configured to abut against the proximal end of the suture anchor with the reduced diameter portion inserted into an inner lumen of the suture anchor, wherein the proximal end of the tip portion and the distal end of the handle portion include complementary male and female mating elements configured to mate the tip portion to the handle portion.

10. The suture anchor system of claim 9, wherein the tip portion is configured to receive multiple strands of an adjustable suture.

11. The suture anchor system of claim 9, wherein the proximal end of the tip portion and the distal end of the handle portion have a snap-fit connection for mating to one another.

12. The suture anchor system of claim 9, wherein the handle portion is cannulated.

13. The suture anchor system of claim 9, wherein the suture-seating groove is formed in an external surface of the suture anchor and extends therealong such that, when the suture anchor is implanted in bone, a first suture positioned within the suture-seating groove can slide freely relative to the suture anchor.

14. The suture anchor system of claim 9, further comprising a first suture extending through the inner lumen of the suture anchor and having a sliding knot formed thereon and positioned within the suture anchor, the first suture having a free end extending from the suture anchor and a collapsible loop portion extending from the suture anchor.

15. The suture anchor system of claim 14, further comprising a second suture in the form of a continuous loop, the second suture being slidably disposed on the collapsible loop portion of the first suture.

16. The suture anchor system of claim 15, wherein the second suture has a diameter that is in a range of about 5 mm to 15 mm.

17. The suture anchor system of claim 14, wherein the sliding knot is disposed within the suture-seating groove.

18. The suture anchor system of claim 14, wherein
   the suture anchor includes a suture-engaging member extending across the inner lumen of the suture anchor, the suture-seating groove located distal to the suture-engaging member, and wherein the first suture extends around the suture-engaging member.

19. The suture anchor system of claim 9, wherein the suture anchor includes a pair of arms at the distal end of the anchor, the arms defining the suture-seating groove therebetween.

* * * * *